(12) United States Patent
Jung et al.

(10) Patent No.: US 6,948,932 B2
(45) Date of Patent: Sep. 27, 2005

(54) DENTAL MODELING AND ARTICULATING SYSTEM

(76) Inventors: Yunoh Jung, 3300 S. 811 E., Sandy, UT (US) 84106; Daniel Yonil Jung, 3300 S. 811 E., Sandy, UT (US) 84106

(*) Notice: Subject to any disclaimer, the term of this patent is extended or adjusted under 35 U.S.C. 154(b) by 0 days.

(21) Appl. No.: 10/606,855

(22) Filed: Jun. 26, 2003

(65) Prior Publication Data

US 2004/0013997 A1 Jan. 22, 2004

Related U.S. Application Data

(60) Provisional application No. 60/454,216, filed on Mar. 12, 2003, and provisional application No. 60/393,160, filed on Jul. 1, 2002.

(51) Int. Cl.⁷ .............................................. A61C 11/00
(52) U.S. Cl. ........................................................ 433/57
(58) Field of Search ............................ 433/60, 54, 57, 433/58, 66, 74, 196, 213; 16/267, 223, 225, 227; D24/1.82

(56) References Cited

U.S. PATENT DOCUMENTS

| | | | | |
|---|---|---|---|---|
| 3,126,120 A | * | 3/1964 | Crate | 220/844 |
| 3,126,632 A | * | 3/1964 | Weissman | 433/60 |
| 4,439,151 A | * | 3/1984 | Whelan | 433/60 |
| 4,466,541 A | * | 8/1984 | Tabler et al. | 206/506 |
| 4,734,033 A | | 3/1988 | Huffman | |
| D305,362 S | | 1/1990 | Huffman | |
| D306,206 S | | 2/1990 | Huffman | |
| 5,046,949 A | | 9/1991 | Richardson | |
| 5,306,145 A | | 4/1994 | Michael | |
| 5,403,185 A | | 4/1995 | Presswood | |
| 5,466,152 A | | 11/1995 | Walter | |
| 5,658,143 A | | 8/1997 | Kuperman | |
| 5,846,076 A | | 12/1998 | Garland | |
| 6,099,305 A | | 8/2000 | Browne et al. | |
| 6,247,927 B1 | | 6/2001 | Walter | |
| 6,318,999 B1 | | 11/2001 | Kim | |
| 6,402,513 B1 | * | 6/2002 | Sim | 433/57 |

* cited by examiner

Primary Examiner—Todd E. Manahan
(74) Attorney, Agent, or Firm—Thorpe North & Western

(57) ABSTRACT

A dental articulating device and method to duplicate at least a portion of a patient's mouth for use in producing a dental prosthesis includes a pair of trays pivotally coupled together by an integral hinge. The hinge includes a pivot axle and a shoulder extending at least partially around the pivot axle and creating two axle portions extending on each side of the shoulder. A pair of fingers are pivotally positioned on opposite sides of the pivot axle and on opposite sides of the shoulder and separated by both the axle and the shoulder.

16 Claims, 13 Drawing Sheets

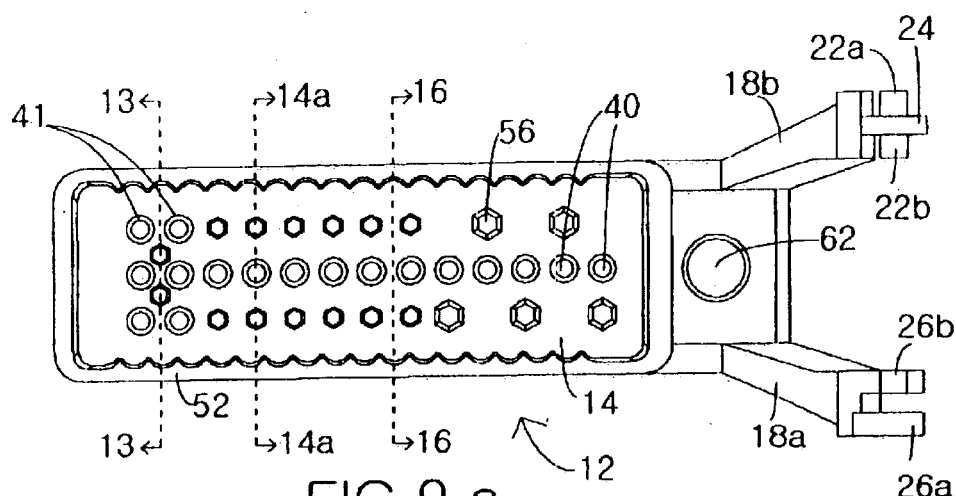
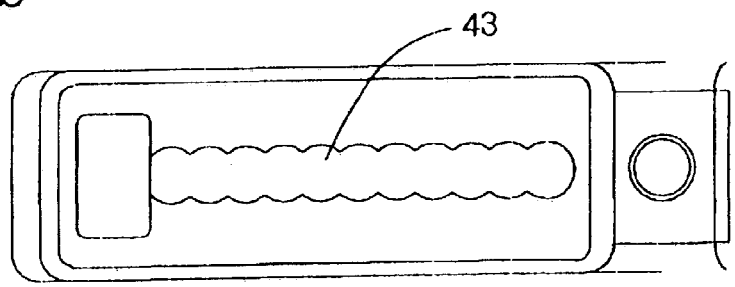
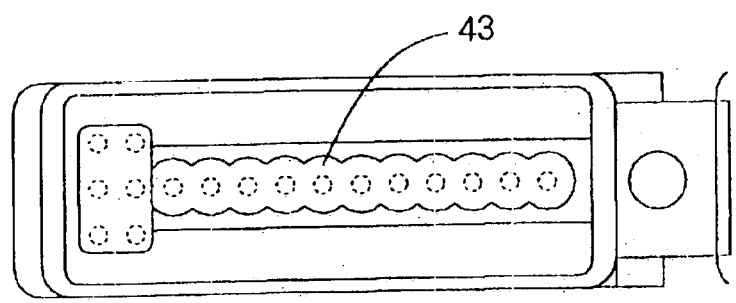

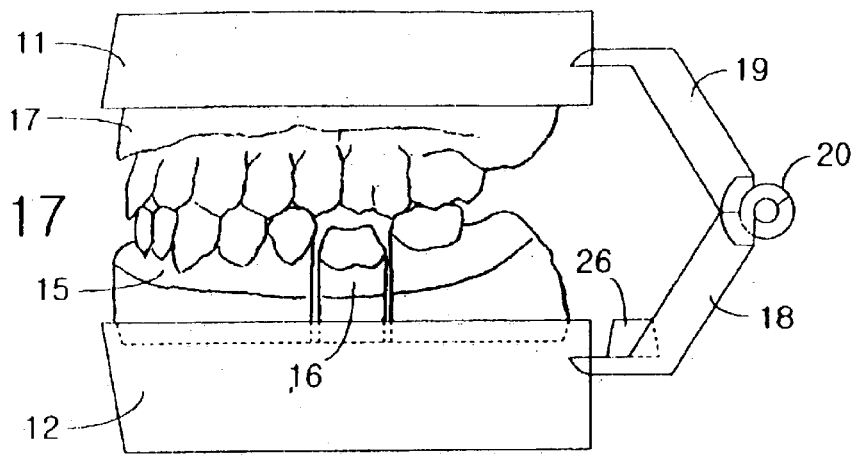
FIG 17
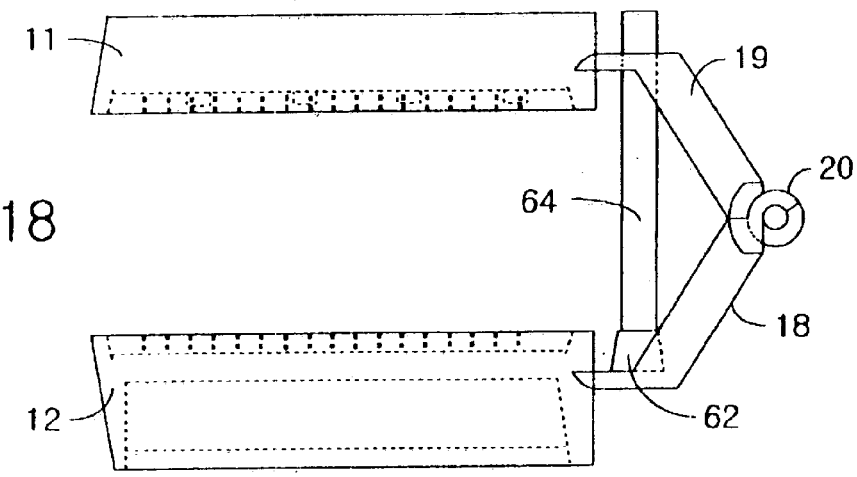
FIG 18
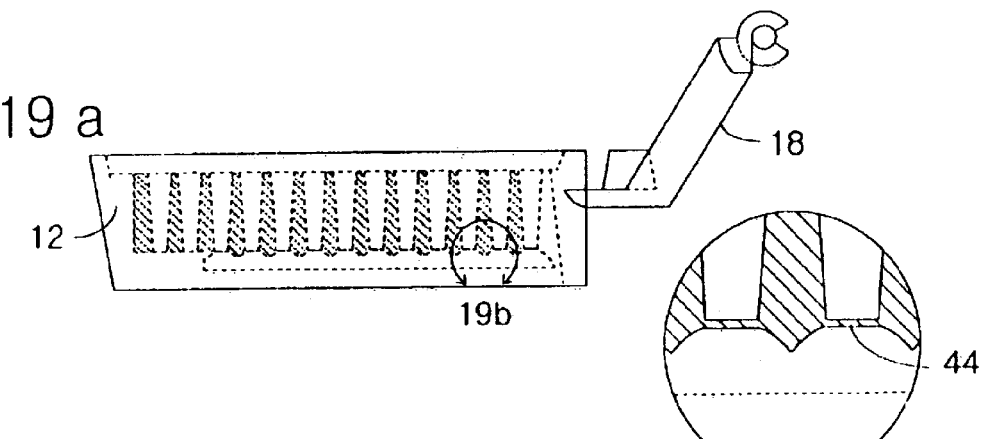
FIG 19 a
FIG 19 b

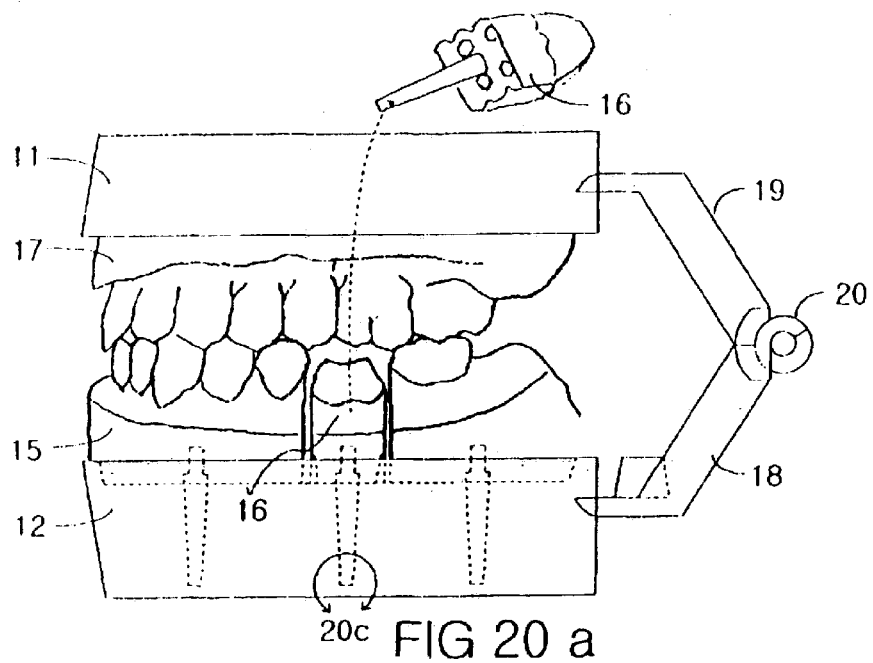
FIG 20 a
FIG 20 b
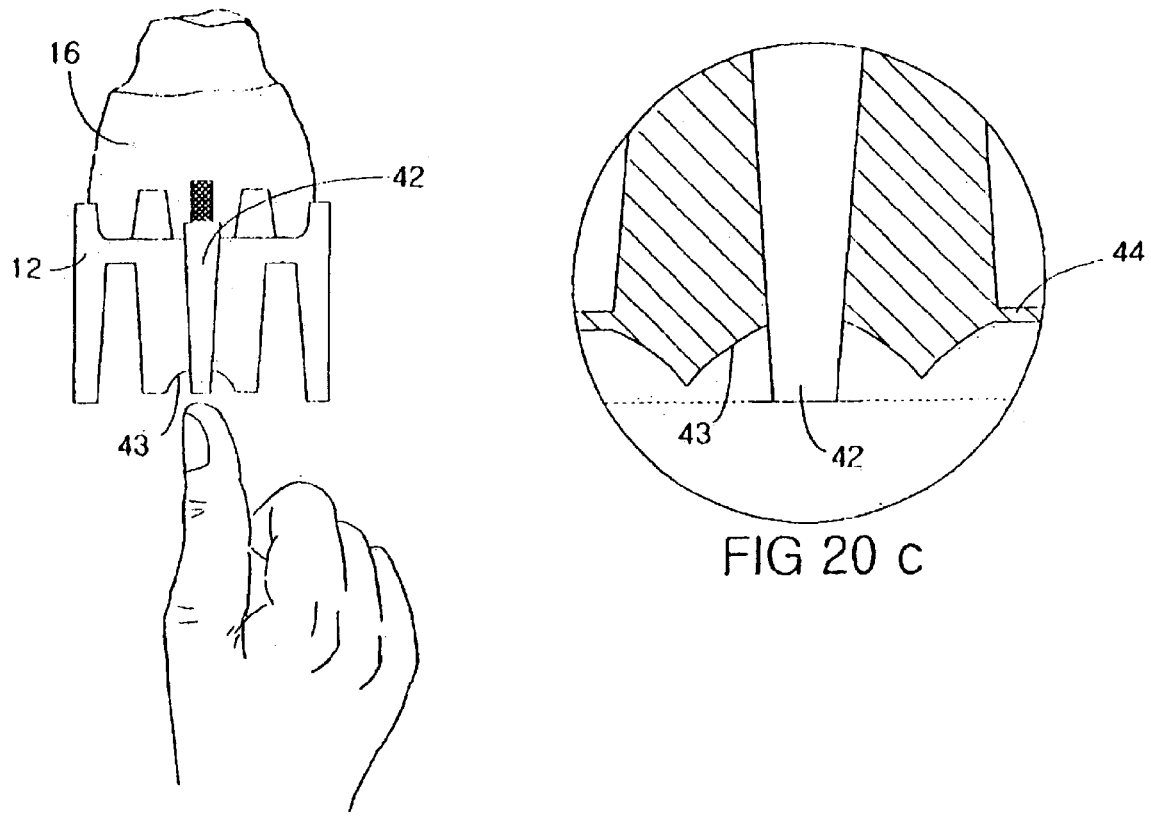
FIG 20 c

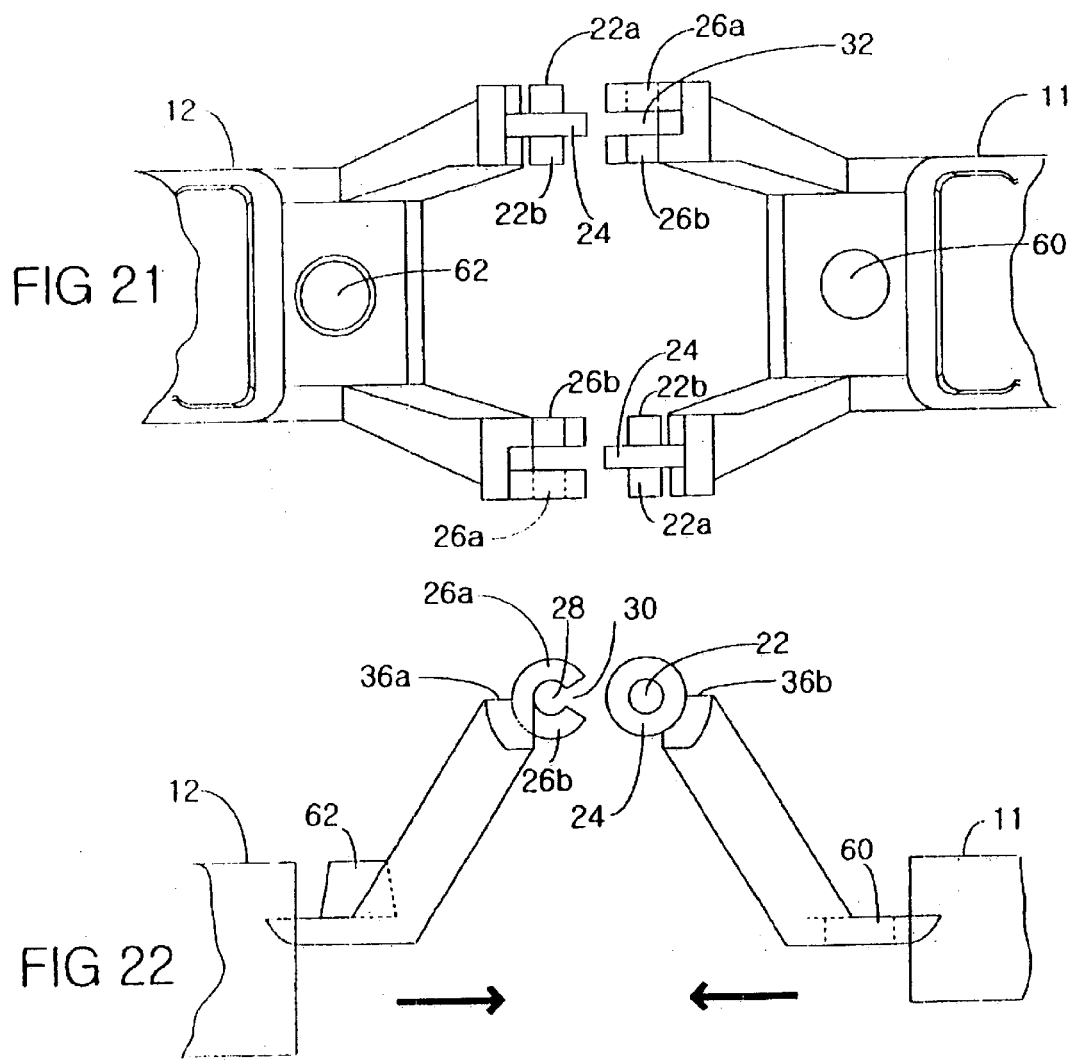

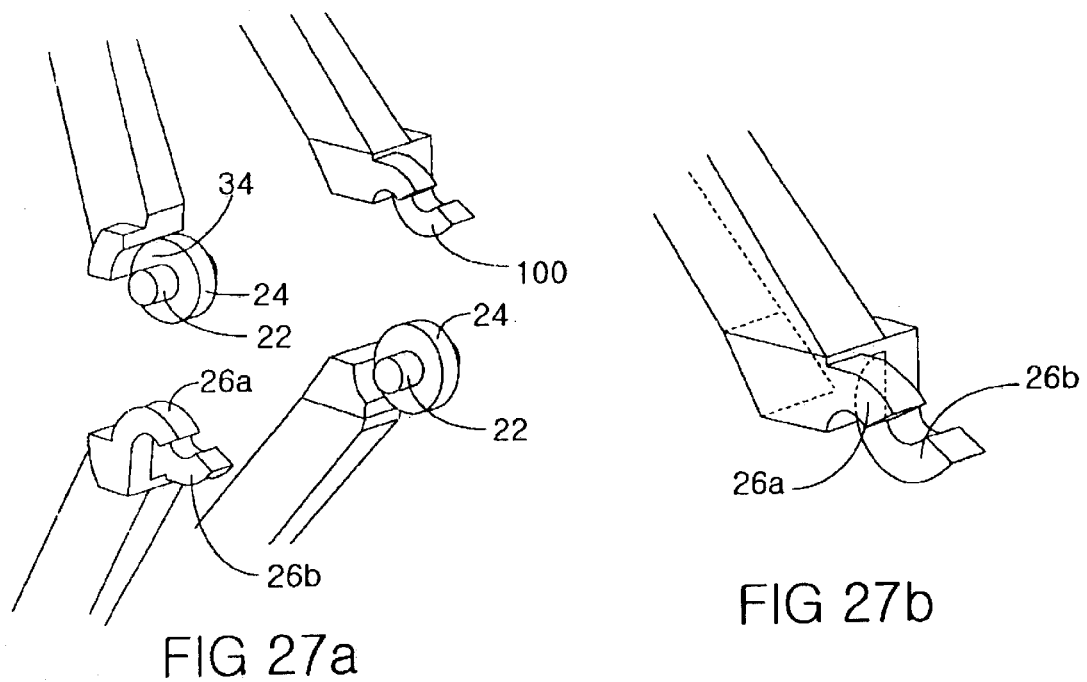
FIG 27a
FIG 27b
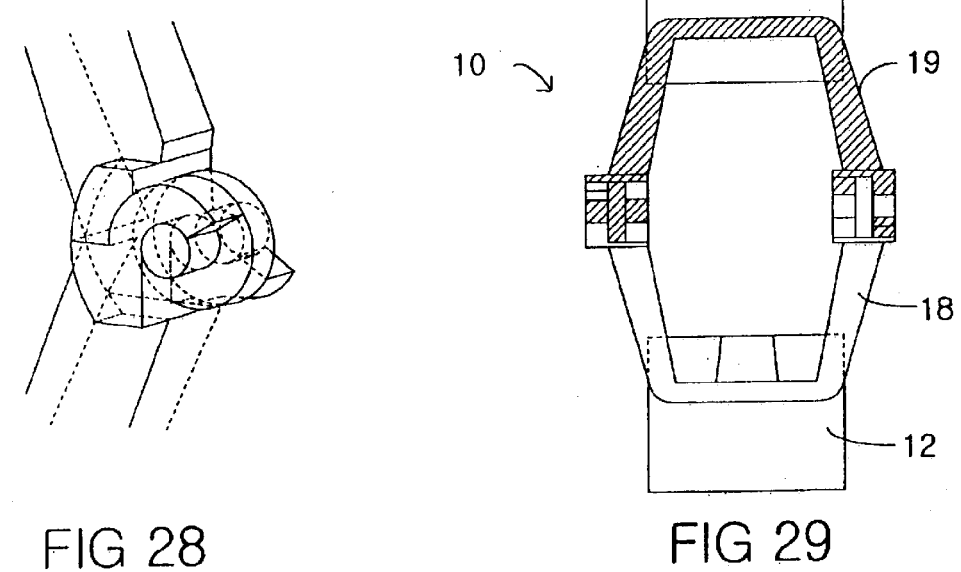
FIG 28
FIG 29

US 6,948,932 B2

DENTAL MODELING AND ARTICULATING SYSTEM

This application claims the benefit of U.S. Provisional Patent Application Nos. 60/393,160, filed Jul. 1, 2002; and 60/454,216, filed Mar. 12, 2003.

BACKGROUND OF THE INVENTION

1. Field of the Invention

The present invention relates generally to dental modeling and articulating systems and methods. More particularly, the present invention relates to a hinge for such a dental modeling and articulating system.

2. Related Art

The production of a dental prosthesis requires the production of a working dental model that is a substantially exact duplication of the patient's mouth, and upon which the prosthesis can be fabricated. Such dental prostheses can include crowns, bridges, caps (substructure) for CAD/CAM production, inlays, onlays and other restorative dental works.

One method of making a dental model is referred to as the "Double Pour Method" or "pindex method." In this method, once the model is poured and allowed time to dry, it is separated and trimmed; then holes are placed in the lower surface of the cast followed by inserting the pin with glue and placing the cast into second-pour stone base. The disadvantages of this process include: time consuming, troublesome dowel pin setup, and the requirement for two pours of casting material to create a base and a die. Moreover, this method often involves guesswork, since this method requires the technician to hand occlude two separate casts manually to set the bite. This guesswork will occasionally result in an inaccurate reproduction of the occlusal relationship of the mandibular and maxilly casts. This inaccurate reproduction will not match the original bites provided by the dentist at the time the negative impression was taken. An example of this method can be found in U.S. Pat. No. 4,734,033. This method can use a separate hinge that is separately attached to the stone bases or models. The hinge can include an adjustable ball-and-socket type connection that is rigidly fixed after the stone bases or models are aligned.

Another method is referred to as the "Single Pour Method" or "wet pinning method." In this method, a plastic tray support member replaces the stone base mentioned above, so the second pour stage is eliminated. As a result, the whole process of making a dental model can be considerably shortened. Moreover, it is possible to mount the case without separating the upper and lower cast from the impression so that the case is mounted with the bite exactly as the impression is provided by the dentist. This "Single Pour Method" or "wet pinning technique" can include two types. The first type is the "open cavity tray type" that 1) can stabilize the prosthesis element being worked on, without shifting, or prevent movement of the prosthesis dies with the help of a notched or arcuate cavity wall which is relatively high; and 2) can eliminate the additional labor of registration pin hole drilling and the pindexing process. The disadvantages of this process include: 1) it can be difficult to control the dies over the entire process of die preparation, wax up, metal finish and porcelain build-up because there is no pin attached at the bottom of the prosthesis dies to hold to work with; 2) initial removal of the entire die from the tray can be difficult because the tray has comparatively high and notched walls necessitating the use of an extra accessory, like a special releasing device, a stand, a mallet etc., and part of the cast can break while being released from the tray; and 3) the initial stage of the wet porcelain build up can be broken because the dies can be seated firmly by a rail or spine that snap fits or clicks into the tray. Examples of such methods can be found in U.S. Pat. Nos. 5,306,145 and 6,099,305.

The second type is the "pin type", where the plastic tray support members have plurality of registration pin holes, and the master die from this system is convenient to hold and work with since there is at least one pin protruding from underneath each segmented die. In addition, the upper cast and lower cast are not separated from the impression until they are articulated by a hinge. Thus, the case is mounted with the bite exactly as the impression provided by the dentist. One disadvantage of this process include excessive holding of the casting material stuck in the registration holes because the semi-liquid model material tends to creep through the registration holes and harden. When the model material hardens, it gets stuck in these holes, making the initial release of the segmented dies from the tray support members difficult. In addition, it may be required to break the dies off the tray forcefully, leaving tiny debris of casting material from the breakage sitting between the dies and the tray during the entire work process, interfering with the proper relationship with the adjacent dies and also the opposing model. Another disadvantage with these methods is that they often have either a flimsy hinge or separate hinges that have to be connected to the main body by harmful glue and hardening accelerator. Examples of this method can be found in U.S. Pat. Nos. 5,466,152 and 6,318,999.

Therefore, important aspects of dental modeling should include: 1) accurate, stable and easy repositioning of the sections of the model to their former relationship with the adjacent dies and also with the opposing model; and 2) the reliable registration of the upper and lower castings with respect to one another.

SUMMARY OF THE INVENTION

It has been recognized that it would be advantageous to develop a dental modeling and articulating system and method that makes accurate, precise and fast dental models from which dental prosthesis elements, such as crowns, bridges, caps (substructure) for CAD/CAM production, inlays, onlays, and other restorative dental works, can be fabricated. In addition, it has been recognized that it would be advantageous to develop a dental modeling and articulating system with tray support members for dental casts and a built-in articulating hinge member that 1) maximizes the work efficiency, 2) provides substantially perfect centric, lateral and protrusive movements, and 3) permits substantial perfect registration of the dental casts.

The invention provides a dental articulator device to duplicate at least a portion of a patient's mouth for use in producing a dental prosthesis. The device includes a pair of trays pivotally coupled together and pivoting with respect to one another between closed and open configurations. In the closed configuration, the trays are opposingly spaced-apart from one another. In the open configuration, the trays are pivoted away from one another. A hinge is integrally formed with the trays and positioned between the trays. On one of the trays, the hinge includes a pivot axle and a shoulder extending at least partially around the pivot axle, creating two axle portions extending on each side of the shoulder. On the other tray, the hinge includes a pair of fingers pivotally positioned both 1) on opposite sides of the pivot axle, and 2) on opposite sides of the shoulder, so that the fingers are separated by both the axle and the shoulder.

In addition, the invention provides a method for forming a dental model. The method includes forming prepped and opposing models of prepped and opposing teeth on lower and upper trays of a dental articulator. The prepped model includes a model of a prepped tooth to receive a dental prosthesis. The opposing model includes a model of an opposite tooth opposite the prepped tooth. The lower and upper trays pivot about a hinge integrally formed with the trays. The hinge includes a first portion with a shoulder circumscribing an axle, and a second portion with opposing fingers movably disposed on opposite sides of the axle and on opposite sides of the shoulder.

Additional features and advantages of the invention will be apparent from the detailed description which follows, taken in conjunction with the accompanying drawings, which together illustrate, by way of example, features of the invention.

BRIEF DESCRIPTION OF THE DRAWINGS

FIG. 2 is a perspective view of an upper tray of the dental articulator of FIG. 1a;

FIG. 3 is a perspective view of the upper tray of the dental articulator of FIG. 1a;

FIG. 4 is a top view of the upper tray of the dental articulator of FIG. 1a;

FIG. 5a is a bottom view of the upper tray of the dental articulator of FIG. 1a;

FIG. 6 is an end view of the upper tray of the dental articulator of FIG. 1a;

FIG. 8 is a perspective view of the lower tray of the dental articulator of FIG. 1a;

FIG. 9a is a top view of the lower tray of the dental articulator of FIG. 1a;

FIG. 9b is a detailed view of the lower tray of FIG. 9a;

FIGS. 10 and 11 are bottom views of the lower tray of the dental articulator of FIG. 1a;

FIG. 12a is an end view of the dental articulator of FIG. 1a;

FIG. 12b is an end view of the lower tray of the dental articulator of FIG. 1a;

FIG. 14a is a cross-sectional end view of the lower tray of FIG. 9a taken along line 14a—14a;

FIG. 14b is a detailed view of the lower tray of FIG. 14a;

FIG. 14c is a cross-sectional end view of a lower tray in accordance with another embodiment of the present invention;

FIG. 17 is a side view of the dental articulator of FIG. 1a, shown with dental casts;

FIG. 18 is a side view of the dental articulator of FIG. 1a;

FIG. 19a is a schematic view of a lower tray of a dental articulator in accordance with an embodiment of the present invention;

FIG. 19b is a detailed view of the lower tray of FIG. 19a;

FIG. 20a is a schematic side view of the dental articulator of FIG. 1a, shown with dental casts;

FIG. 20b is a schematic cross-sectional end view of a lower tray of the dental articulator of FIG. 1a, shown with a prosthesis die;

FIG. 20c is a detailed view of a lower tray of the dental articulator of FIG. 20a;

FIG. 21 is a partial exploded top view of the dental articulator of FIG. 1a;

FIG. 22 is a partial exploded side view of the dental articulator of FIG. 1a;

FIG. 23 is a partial perspective view of the lower tray the dental articulator of FIG. 1a;

FIG. 24 is a partial exploded side view of the dental articulator of FIG. 1a;

FIG. 27a is a partial exploded perspective view of the dental articulator of FIG. 1a;

FIG. 27b is partial perspective view of the dental articulator of FIG. 1a;

FIG. 28 is a partial perspective view of the dental articulator of FIG. 1a;

FIG. 29 is a schematic end view of the dental articulator of FIG. 1a;

FIG. 30b is a cross-sectional end view of the tray of FIG. 30a;

DETAILED DESCRIPTION

Figure 1A:
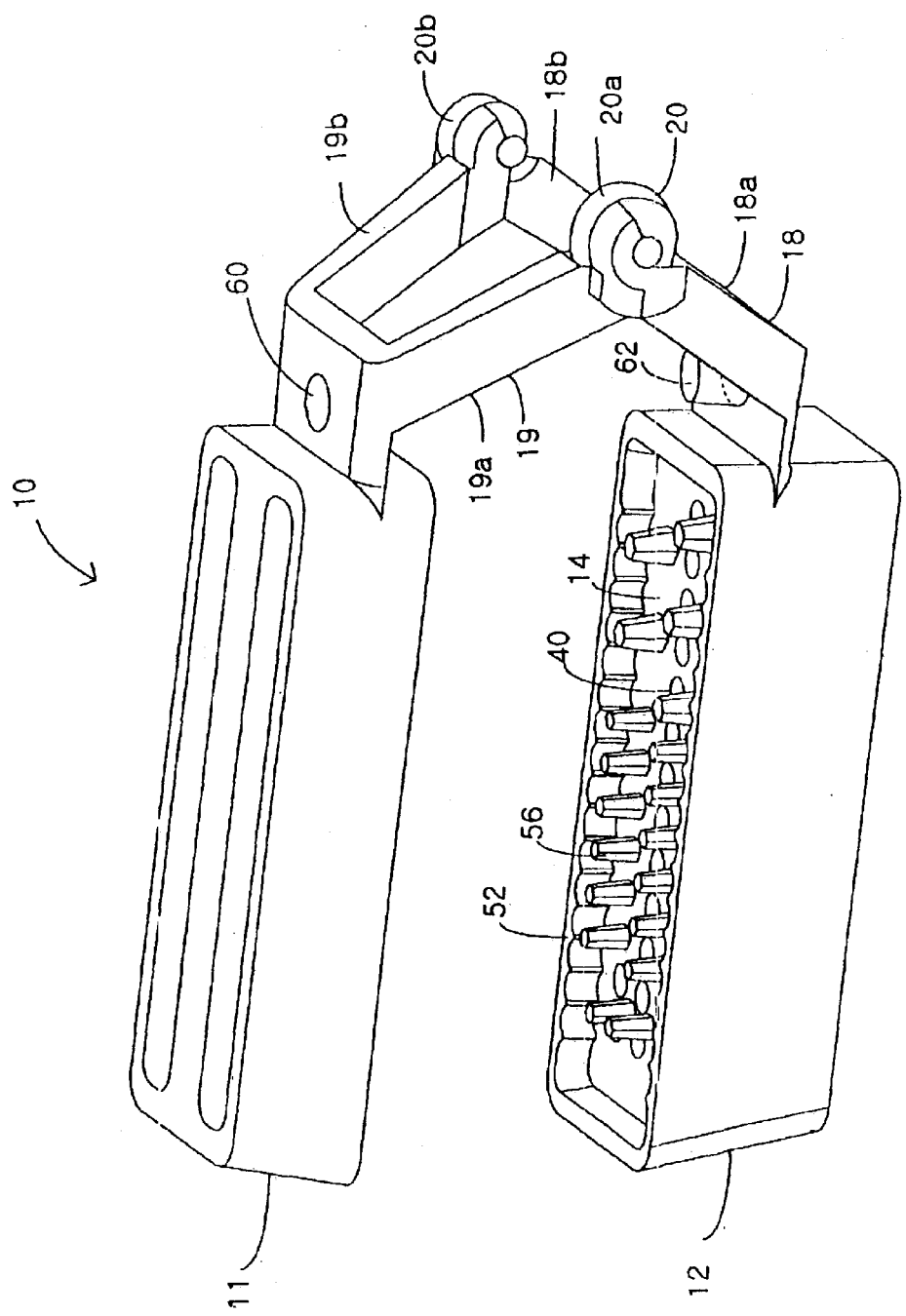
FIG. 1a is a perspective view of a dental articulator of a dental modeling system in accordance with an embodiment of the present invention, shown in a closed configuration.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

As illustrated in FIGS. 1–29, a dental modeling and articulating system or device, indicated generally at 10, and its component parts, in accordance with the present invention is shown for use in producing a dental model that is a substantial duplicate of a patient's mouth for use in the production of dental prostheses. Such dental prostheses can include crowns, bridges, caps (substructure) for CAD/CAM production, inlays, onlays and other restorative dental works. The dental modeling and articulating system 10 includes a pair of trays, such as upper and lower trays 11 and 12, that are pivotally coupled together. The trays 11 and 12 have die receiving surfaces, such as respective upper and lower die receiving surfaces 13 and 14.

The trays 11 and 12, or die receiving surfaces 13 and 14, receive dental casting material, and dies or models of a patient's teeth. The lower tray 12 and lower die receiving surface 14 can receive a prepped model 15 or lower cast (FIGS. 17 and 20a) of one or more prepped teeth of a patient. The prepped model 15 can include a model of a prepped tooth, or prosthesis die 16 (FIGS. 17 and 20a), to receive a dental prosthesis. Thus, the lower tray 12 and lower die receiving surface 14 receive the prepped model of the tooth that will be worked on. The upper tray 11 and upper die receiving surface 13 can receive an opposing model 17 or upper cast (FIGS. 17 and 20a) of one or more opposing teeth of a patient that oppose the prepped teeth. The opposing model 17 can include a model of an opposite tooth opposite the prepped tooth.

It should be noted that the designation or description of the trays and die receiving surfaces as being "upper" and "lower" does not necessarily correspond to the patient's upper and lower teeth. The lower tray can be the working or prepped tray and can receive the prepped model 15 (FIGS. 17 and 20a), which can correspond to either the patient's upper or lower teeth. As the working or prepped tray, it is typically most convenient to position the tray as the lower tray. Similarly, the upper tray can be the opposing tray and can receive the opposing model 17 (FIGS. 17 and 20a). It will be appreciated that the upper and lower trays can have different configurations, as shown, or can have similar or the same configurations. Because a majority of dental cases require prosthetics or the like for only the upper or lower side of the mouth, it is typically only necessary to have one lower or working tray. In cases where both the upper and lower side of the mouth require prosthetics or the like, then two lower trays can be coupled together.

Figure 1B:
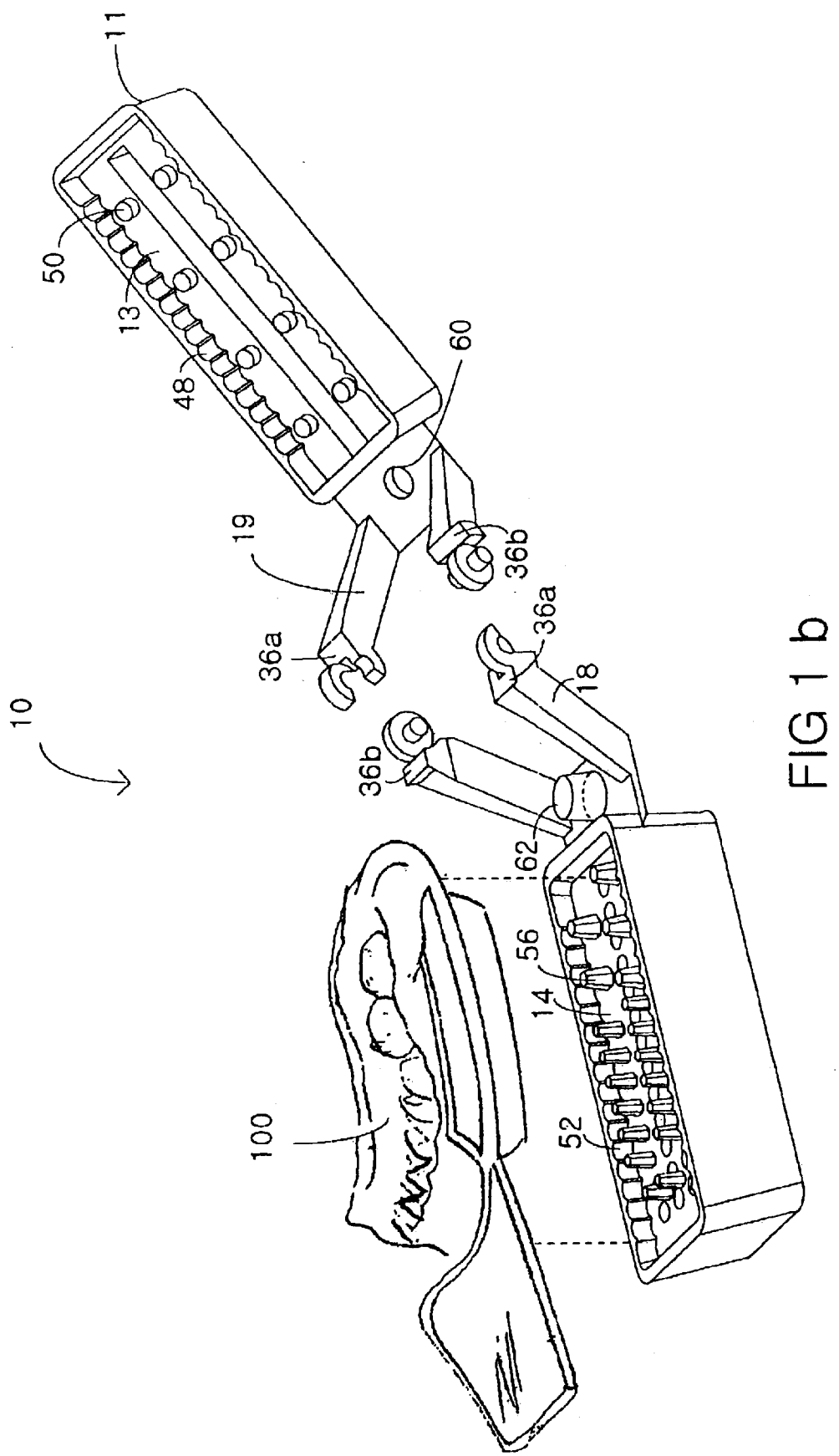
FIG. 1b is an exploded perspective view of the dental articulator of FIG. 1a, shown in an open position and with a negative impression of a patient's teeth.

The trays 11 and 12 can pivot with respect to one another between a closed configuration and an open configuration. In the closed configuration, the trays 11 and 12 generally oppose one another and are spaced apart from one another, as shown in FIG. 1a. The die receiving surfaces 13 and 14 oppose one another in the closed configuration. In the open configuration, the trays 11 and 12 can pivot away from one another, as shown in FIG. 1b. The closed configuration corresponds to, or models or imitates, a patient's closed mouth, and the dies or models of the patient's teeth close against one another (as shown in FIG. 17). The open configuration allows the dies or models of the patient's teeth to be separated for producing dental prostheses and the like. In addition, the trays 11 and 12 can be detachably connected to allow the trays to be separated. The trays may be provided separately (as shown in FIG. 1b), and connect during or before use.

The trays 11 and 12 can include a pair of arms, or lower and upper arms 18 and 19, each extending from one of the trays to a hinge 20. Thus, the arms 18 and 19 can maintain the trays 11 and 12 in a spaced-apart relationship in the closed configuration. The lower arm 18 can extend upwardly and rearwardly, while the upper arm 19 can extend downwardly and rearwardly. Thus, the hinge can be positioned behind the tray. In addition, the lower arm 18 can include a pair of lower arms 18a and 18b, and the upper arm can include a pair of upper arms 19a and 19b. Thus, the device 10 can include a pair of hinges 20a and 20b, each disposed between a different pair of arms. The lower arms 18a and 18b and the upper arms 19a and 19b can also extend laterally outwardly from the trays 11 and 12 so that the pair of hinges 20a and 20b are spaced-apart from one another. The spaced-apart hinges 20a and 20b can provide additional stability to the movement of the trays. The trays and arms can be integrally formed.

The trays 11 and 12, and the arms 18 and 19, are pivotally and detachably connected by the hinge 20. The hinge 20 is positioned between the trays 11 and 12, and between the arms 18 and 19. In addition, the hinge 20 is integrally formed with the trays 11 and 12, and thus with the arms 18 and 19. A portion of the hinge 20 can be carried by each tray or arm. Thus, the hinge can be a two-part hinge with one part formed with the lower tray and lower arm, and the other part formed with the upper tray and upper arm. In addition, the hinge 20 or parts thereof can snap together for use (as shown in FIG. 1a). The hinge 20 or trays 11 and 12 can be separated if necessary (as shown in FIG. 1b). The arms 18 and 19 and hinge 20 allow the device 10 to mimic or model the open and closing function of a mouth.

Referring to FIGS. 21–29, the hinges 20a and 20b each can include a pivot axle 22a and 22b. The pivot axles can be aligned or collinear. A shoulder 24 can extend at least partially around each pivot axle 22a and 22b dividing the pivot axle and creating two axle portions extending from each side of the shoulder 24. The shoulder 24 can circumscribe or extend entirely around the axle 22a and 22b, as shown. In addition, the shoulder 24 can extend between the arm and the axle to attach the axle to the respective arm. The axle and shoulder can form a first part of the hinge. The second part of the hinge can include a pair of fingers 26a and 26b that extend from another arm and that pivotally engage and hold the first part of the hinge. The fingers 26a and 26b can grip both the axle 22a and 22b and the shoulder 24. Thus, the fingers 26a and 26b can be pivotally positioned on opposite sides of the axle 22a and 22b, and on opposite sides of the shoulder 24. The fingers 26a and 26b can bear against the axle and the shoulder in a slidable fashion. Thus, the hinge provides a solid or firm feel, and resists undue movement between the trays. It has been found that such a hinge 20 permits limited movement of the upper tray 11 with respect to the lower tray 12 to simulate the natural movements of the human jaw, including centric, lateral and protrusive movements.

The fingers 26a and 26b, or inner surfaces thereof, can be arcuate or curved with the curvature oriented in a plane orthogonal to the pivot axle. Thus, the fingers can curve about the axle. In addition, the fingers 26a and 26b can define a pivot opening 28 therebetween to receive the pivot axle 22a and 22b. Thus, the pivot opening 28 can be circular to receive the circular shape of the pivot axle. Furthermore, a gap 30 can be formed between distal ends of the fingers 26a and 26b and can define an entrance to the pivot opening 28. The gap 30 can be narrower than the pivot opening 28 so that the axle 22a and 22b can be inserted through the gap 30 and into the pivot opening 28, and the axle can be maintained in the pivot opening. The gap 30 can be tapered, or can narrow, with a wider entrance to receive the axle. In addition, the fingers can be relatively flexible, so the size and material of the fingers can allow the distal ends of the fingers to separate at the gap 30 to allow the axle to be pressed into and pulled out of the pivot opening 28 under force, but maintain the axle in the pivot opening during use. In addition, the fingers 26a and 26b can be laterally spaced-apart to form a space 32 therebetween to receive the shoulder 24 therein.

Figure 24:
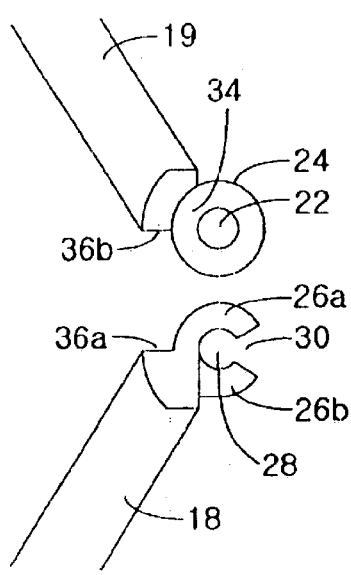
Figure 26:
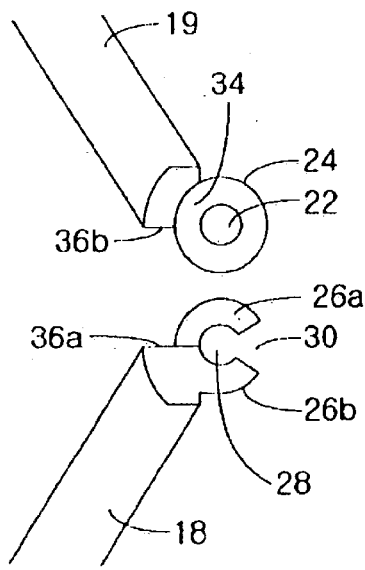
FIG. 26 is a partial exploded side view of another hinge part in accordance with the present invention.

A curved channel 34 can circumscribe at least a portion of the pivot axle 22a and 22b, as shown in FIG. 24. As the trays 11 and 12 pivot with respect to one another, one of the fingers 26a or 26b can move within the curved channel 34. It is believed that the curved channel provides further support and rigidity to the hinge. The finger can be in the channel 34 in the closed configuration to hold the finger in the channel, but can be out of the channel in the open configuration so that the trays can be separated.

Stops 36a and 36b can be formed on the hinge 20 or the arms 18 and 19 and positioned to abut when the trays are in the closed configuration to maintain the trays in the proper position.

The hinge 20, or parts thereof, can be formed integrally with the trays 11 and 12 and arms 26a and 26b, thus eliminating the usage of harmful glues and hardening accelerators.

The hinge 20 allows the upper tray 11 to be movable toward and away from the lower tray 12. Thus, with the dental casts 15 and 17 on the lower and upper trays (as shown in FIGS. 17 and 20a), it is possible to simulate the opening and closing movement of a patient's jaw. In addition, it is possible to pivot the upper tray 11 away from the lower tray during work on the lower cast 15.

Figure 2:
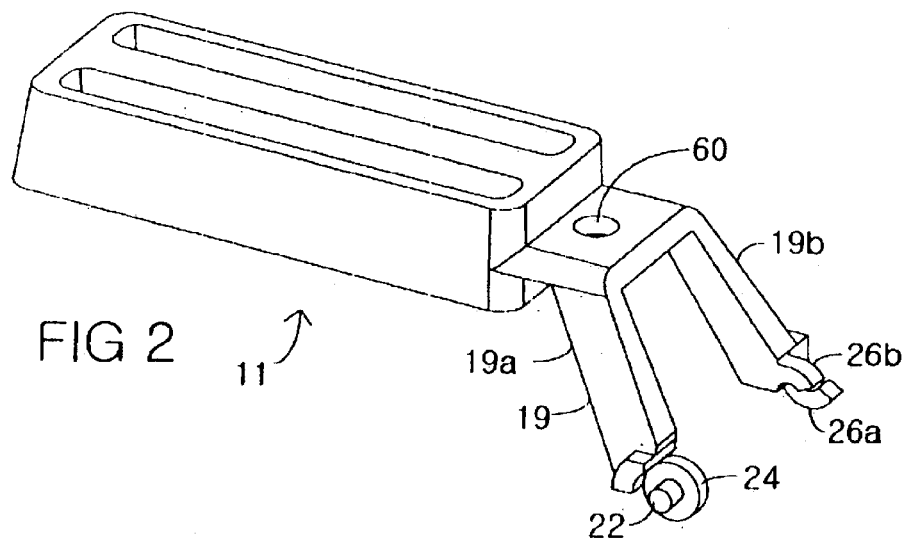
Figure 3:
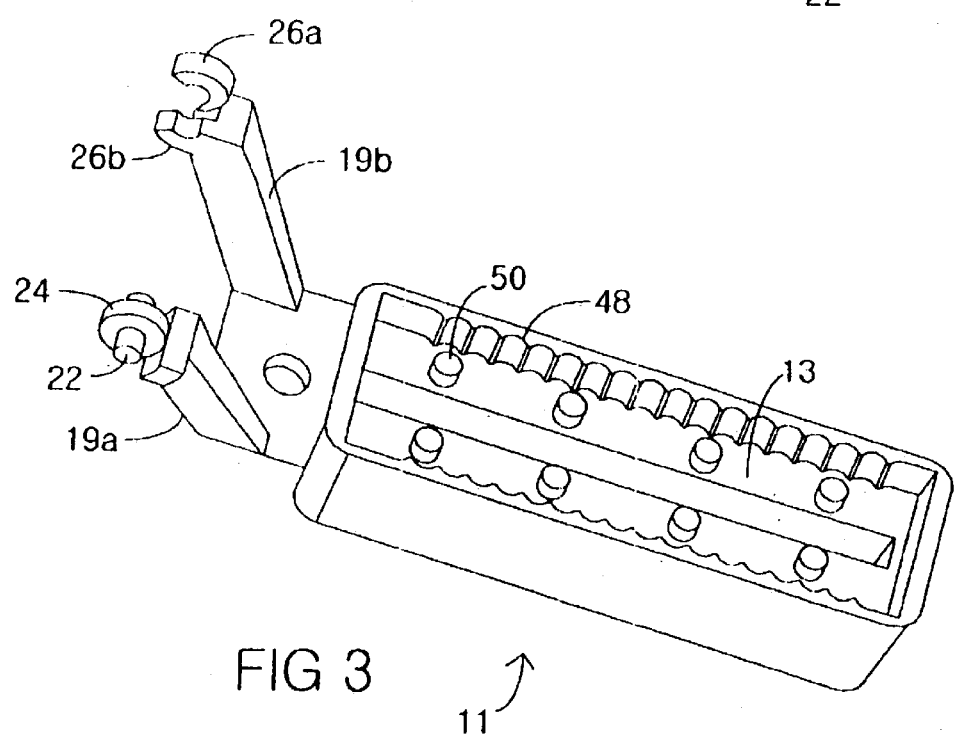
Figure 4:
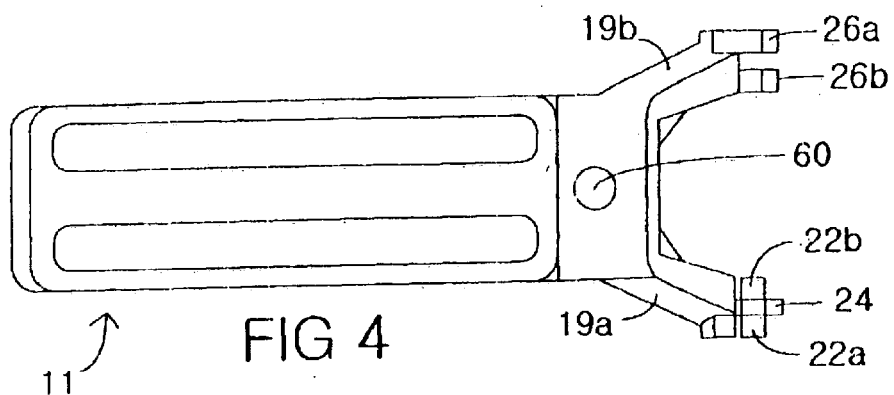
Figure 5A:
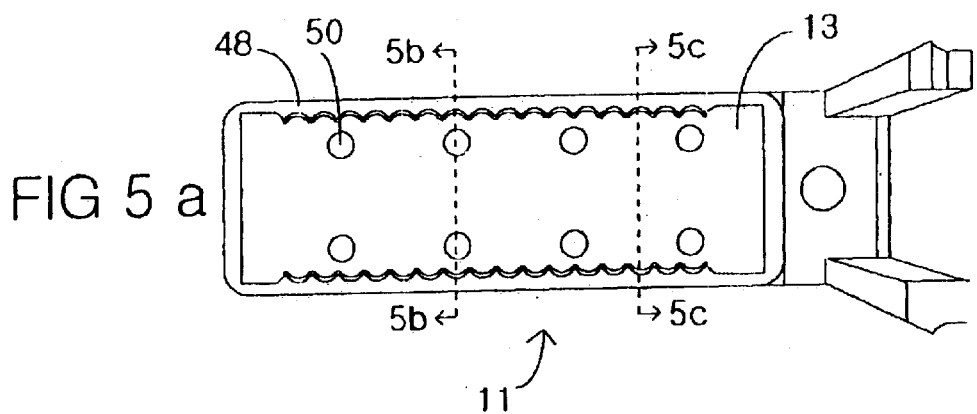
Figure 5B:
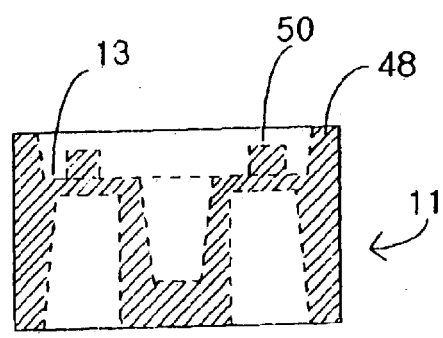
FIGS. 5b and c are cross sectional end views of the upper tray of FIG. 5a taken along lines 5b—5b and 5c—5c respectively.
Figure 5C:
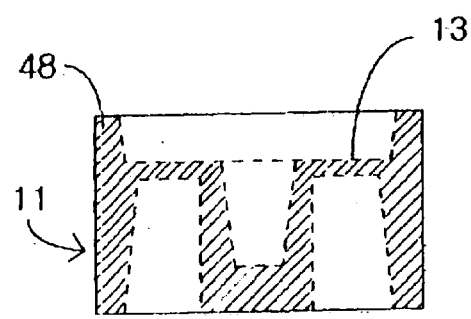
Figure 6:
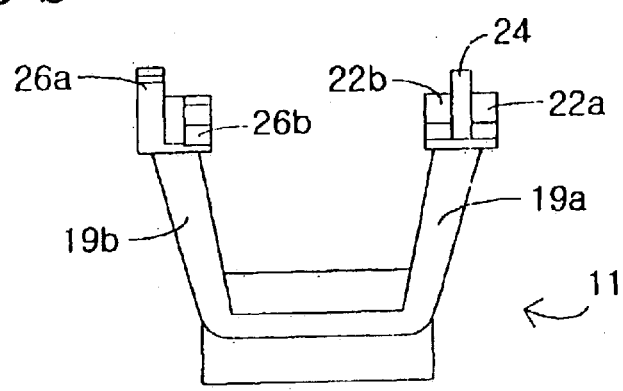
Figure 7:
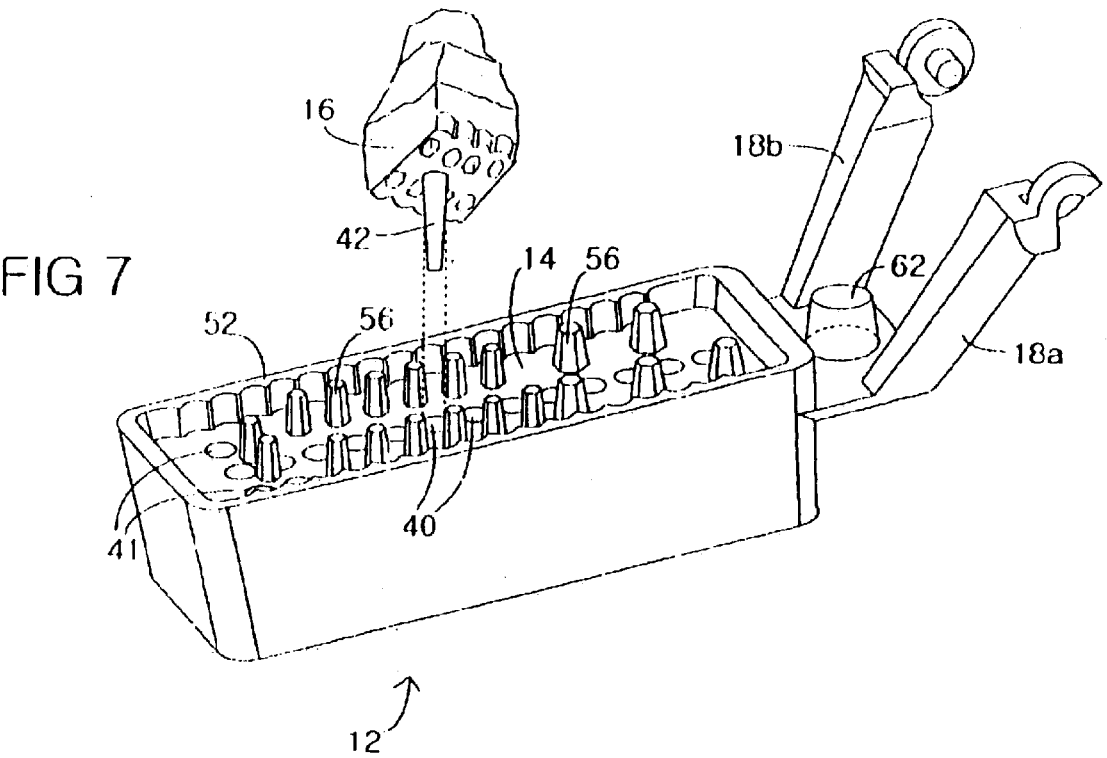
FIG. 7 is a perspective view of a lower tray of the dental articulator of FIG. 1a, shown with a prosthesis die.
Figure 8:
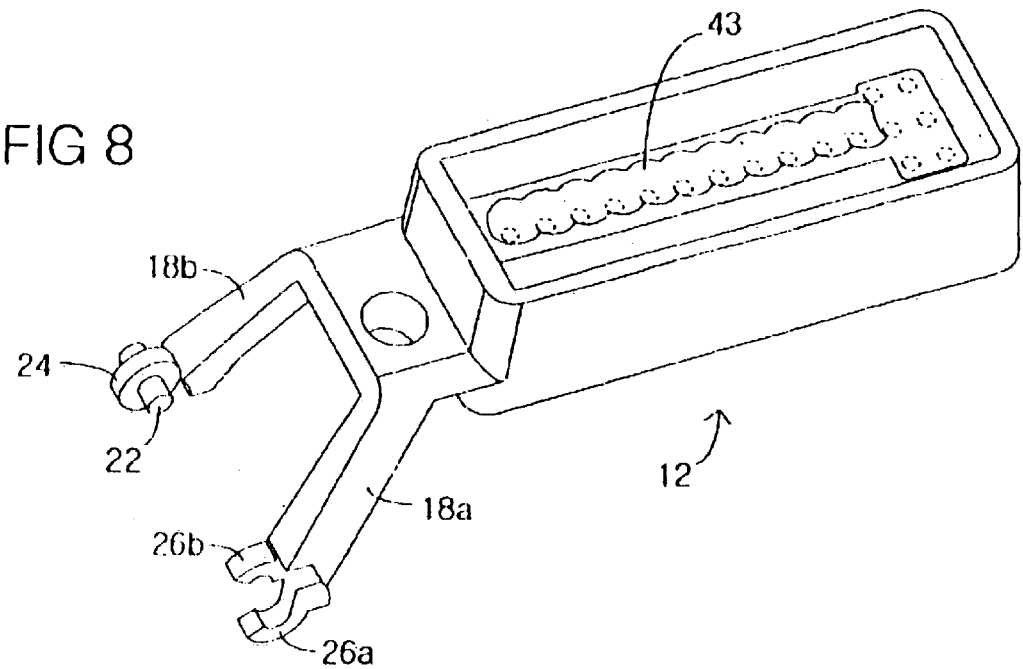
Figure 12:
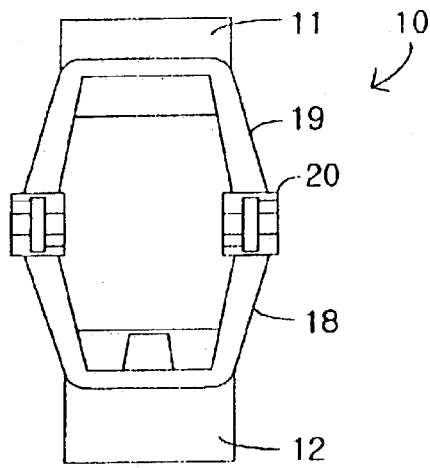
Figure 12:
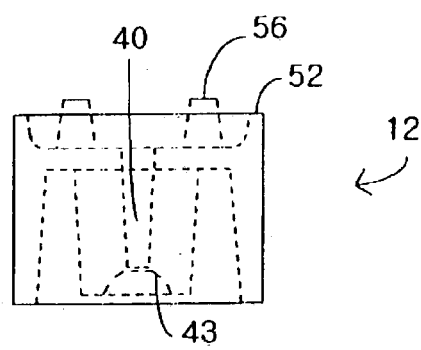
Figure 13:
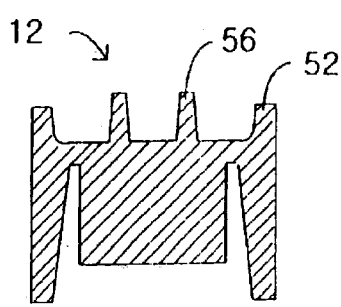
FIG. 13 is a cross-sectional end view of the lower tray of FIG. 9a taken along line 13—13.
Figure 14:
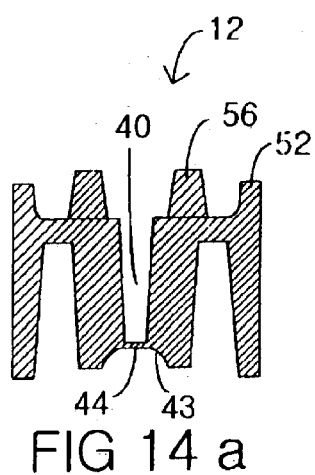
Figure 14:
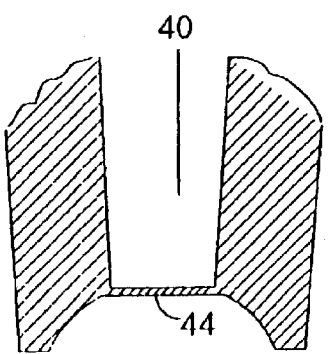
Figure 14:
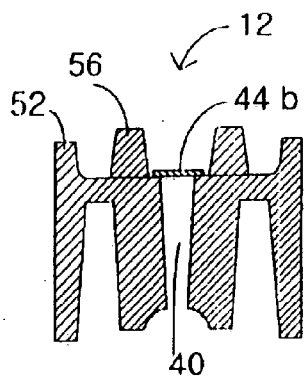

The lower arms 18a and 18b can each have different or opposite parts of the hinge 20, as shown in FIGS. 7 and 8. For example, one of the arms 18a can include the pair of fingers 26a and 26b, while the other of the arms 18b can include the pivot axle 22 and shoulder 24. Similarly, one of the upper arms 19a can include the pivot axle 22 and shoulder 24, while the other of the arms 19b can include the pair of fingers 26a and 26b, as shown in FIGS. 2 and 3. Thus, a pair of lower trays 12 can be coupled together.

In addition, one or both or the trays, such as the lower tray 11, can include an array of registration pin holes 40 for receiving registration pins 42 that are secured to the casts, as shown in FIG. 7. The registration pin holes 40 can be arrayed in a single row aligned with a longitude of the tray, and positioned in a center of the tray. The registration pin holes 40 and the registration pins 42 can be slightly tapered to help seat and secure the pins in the holes so that there is substantially no play or movement between the two. The registration pin holes taper inwardly extending into the tray from the die-receiving surface. The registration pin holes 40 can be evenly spaced and arranged in rows extending parallel to the rows of registration struts described below. Additional registration pin holes 41 can be formed at a free end of the tray to embrace either the left or right side of the upper and lower dental arch. The additional registration pin holes 41 at the free-end can be configured for curved aspects of the impression for anterior teeth.

Figure 15:
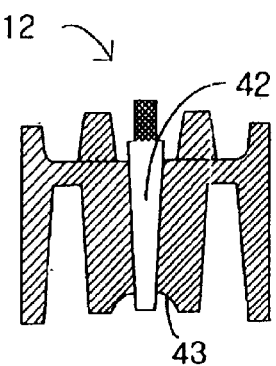
FIG. 15 is a cross-sectional end view of the lower tray of FIG. 9a, shown with a registration pin.
Figure 16:
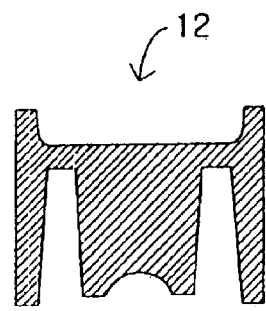
FIG. 16 is a cross-sectional end view of the lower tray of FIG. 9a taken along line 16—16.
Figure 23:
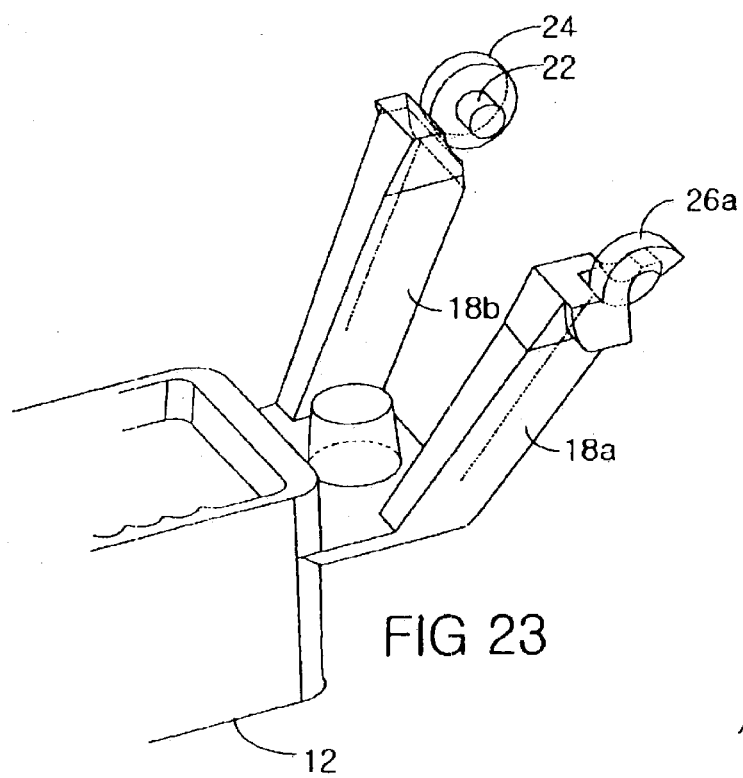
Figure 25:
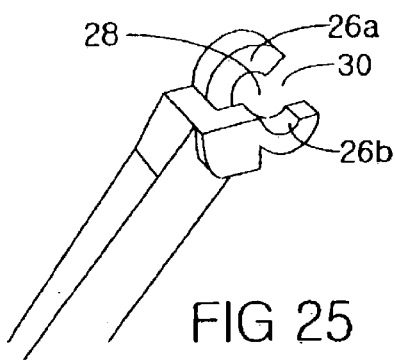
FIG. 25 is a partial perspective view of another hinge part in accordance with the present invention.

Referring to FIGS. 15 and 20, a registration pin 42 can be placed into a registration pin hole 40 or 41. The registration pin 42 can be a brass dowel pin with a head portion that has a knurled outer surface that can be embedded into the molded cast or model 15 (FIGS. 17 and 20a). The other end of the registration dowel pin can be a base portion that has a smooth outer cylindrical or frusto-conical surface that is inserted into and removed from the registration pin hole 40 or 41. FIG. 20 shows a side view wherein the tray support members 11 and 12 have been pivotally rotated in relationship to one another. Registration pins 42 have been placed in the registration pin holes 40 and 41. Casting material has been poured into place on the bed of the tray.

Referring to FIGS. 8, 10, 11, 14–16 and 20, rounded and recessed thumb indentations 43 can be centered at a bottom of the registration pin holes 40, or near the bottom of the tray. The thumb indentations 43 can have a depth to receive a distal end of the registration pin 42 when inserted into the registration pin hole 40. The thumb indentations 43 accommodate the finger or thumb tips of the technician's hand to push the pins 42 from the registration pin holes 40, and thus push the prosthesis die 16 from the tray. The thumb indentations 43 allow the technician to push up softly and smoothly on the tip of the registration pin 42, thereby easily removing the prosthesis die 16 and prosthesis work thereon. The thumb indentations 43 can be especially useful when, at the initial stage of porcelain build up which is still in wet condition, the prosthesis die 16 needs to be removed from the tray, as well as for subsequent engagement and disengagement of the prosthesis die 16 to and from the lower tray that is being worked on. It will be understood that when the wet porcelain is not in solid condition, the porcelain is fragile. The thumb indentations 43 facilitate the removal of the registration pins 42 from the registration pin holes 40, and thus the removal of prosthesis work from the prosthesis die 16 (or working/master die) at an initial stage of porcelain build up.

Referring to FIGS. 14a and 14b, a thin membrane 44 advantageously can be disposed across one or more of the registration pin holes 40. The thin membrane 44 can close off the registration pin holes 40 or 41 and resist dental casting material from substantially filling the registration pin holes, as discussed below. The thin membrane 44 can include a material and thickness that is breakable or piercable by the registration pin 42 when inserted into the registration pin hole, and/or forced against the thin membrane. The membrane 44 can be of sufficient thickness to close the holes 40 and 41, and can be of sufficient thinness to be easily pierced by inserting and pushing the registration pin 42 with finger tips from the side of the die-receiving surface to the bottom surface of the tray. Alternatively, a tool or the like can be used to push the pin through the membrane. The thin membrane can have a thickness in the range of 0.002~0.003 inches (0.06~0.08 mm).

In addition, the thin membrane 44 can be positioned, and the registration pin 42, can be sized, so that the registration pin 42 extends through the thin membrane 44. The thin membrane 44 can be formed of the same material as the tray, and can be formed integrally with the tray. The thin membrane 44 can be positioned near a bottom of the registration pin holes 40 and 41. For example, the thin membrane 44 can be positioned between the registration pin holes 40 and the thumb indentations 43. Such a location near the bottom of the registration pin holes 40 and 41 can facilitate manufacture during an injection molding process.

Figure 30A:
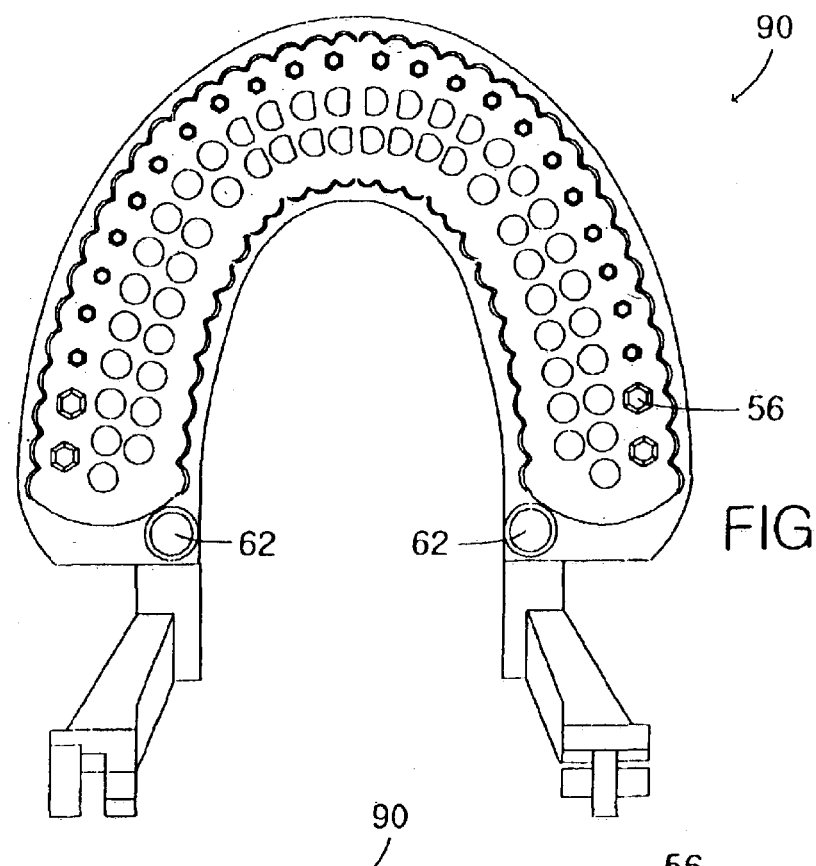
FIG. 30a is a top view of another dental tray of another dental articulator of another dental modeling system in accordance with another embodiment of the present invention.
Figure 30B:
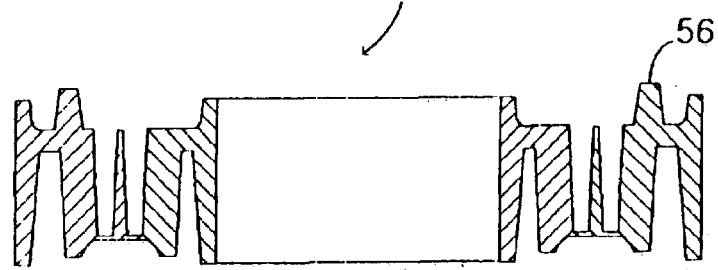
Figure 30C:
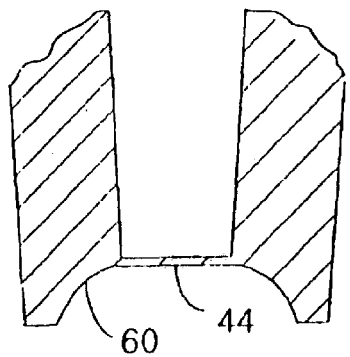
FIG. 30c is a detail view of the tray of FIG. 30b.
Figure 30D:
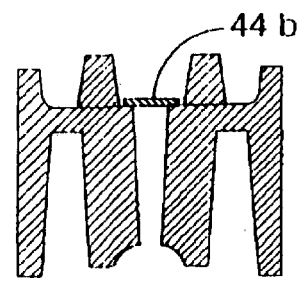
FIG. 30d is a cross-sectional end view of another embodiment of a tray in accordance with the present invention.

Alternatively, as shown in FIGS. 14c, 19a and 30d, the thin membrane can be positioned as desired, such as at a top of the registration pin holes 40 and 41, and at the die receiving surface 14. For example, a thin membrane 44b can be separately formed from the tray, and attached to the tray. Such a thin membrane 44b can be attached to the die receiving surface at the top of the registration pin holes 40 and 41. The thin membrane 44b can be attached by adhesive, sonic welding, etc.

The thin membrane 44 or 44b can close the registration pin holes 40 and 41 and can provide a distinct advantage over open registration pin holes. For example, open registration pin holes allow the semi-liquid casting material to creep into the holes when the negative impression filled with this casting material is inverted onto the tray. The casting material can get stuck in the hole when it hardens, making the initial release of the segmented dies from the tray support members an arduous and difficult job. The closed registration pin holes, however, are closed at one end by a thin membrane, creating an air pocket in the hole when the impression filled with casting material is inverted onto the tray. The air pocket resists the casting material from creeping into the registration pin hole, thus making the removal of the dies easy and clean, and eliminating the initial die breakage off the tray. The absence of the tiny debris of casting material from the initial breakage, and from subsequently repeated engagement and disengagement of the prosthesis dies to the tray, keeps the die receiving surface of the tray clean at all times, and allows positive, accurate, and solid re-registration of the segmented dies onto the tray support member, thus resulting in proper spatial relationship of the segmented dies with respect to the remainder of the dental cast.

As stated above, the lower tray 12 can be the working tray, or the tray to receive the prosthesis die 16 which is a model of the tooth to be worked on; while the upper tray 11 can be the opposing tray that receives the opposing model 17. Thus, the lower tray 12 can receive the model of either the upper or lower teeth of the patient. The trays can have an elongated, rectangular shape to receive models of one side of a user's teeth. Referring to FIG. 1b, the upper tray 11 can be simpler in design, structure and function compared to lower tray 12. Cases that require prosthesis dies on both the upper and lower teeth at the same time are rare. Clinically, less than 3 cases out of 100 cases need prosthesis work for both upper and lower teeth at the same time. If prostheses must be prepared for both upper and lower teeth, then two lower trays 12 can be connected together. Otherwise, a simpler upper tray 11 will often suffice to hold the upper cast or opposing model with a tight grip. The upper die-receiving surface 13 of the upper tray 11 can have a recessed trough formed therein with a perimeter wall 48 extending around the tray and forming the trough. Gripping struts 50 can be formed on the surface 13 of the upper tray 11 to help hold the cast with internal stability after the casting material hardened.

As show in FIGS. 1a, 7 and 20a, the lower tray 12 can include a trough formed by a perimeter wall 52 and into which casting material can be poured. The perimeter wall 52 (and 48) can have a wavy profile, or an inner surface with a wavy cross-section. The wavy profile can include a plurality of curved or arcuate indentations to form curved or arcuate protrusions in the casting material or models. It has been found that the curved, convex protrusions in the casting material are less susceptible to breaking or chipping. Broken or chipped portions of the casting material can inadvertently lodge between the tray 12 and the sectioned dies 15–16 preventing proper repositioning of the sectioned dies. The rounded walls can provide a distinct advantage over notched-edge or saw-like serrations by reducing the breakage and wear from the repeated re-positioning of the prosthesis dies while being worked on. In addition, the wall 52 maintains and holds the dies while offering minimal retention resistance, thereby eliminating the use of extra accessories like releasing devices, stands, mallets, etc. that are needed in other systems.

Referring to FIGS. 7 and 9a, the angle of the wall 52 in the lower tray 12 can be wider for easier release of a segmented die 15–16 (FIG. 20a). In addition, the lower tray 12 can include registration struts 56 disposed on the die-receiving surface 14 and arrayed from the free end to the hinged end. The registration struts 56 can have a hexagonal cross-section. It has been found that the hexagonal cross-section of the registration struts 56 can help maintain the proper alignment of the segmented die 15–17. Smaller struts can be located near the free end, while larger struts can be located near the hinge end. The smaller struts can be smaller in diameter than the registration pin holes. The registration struts can taper inwardly and upwardly along a length of the strut, and can form internally retentive concavities in the cast. The center of each strut can be laterally aligned with a center of corresponding and adjacent registration pin holes. The alignment of the struts with the registration pin holes allow each segmented cast or die to have at least one pin, and one or more struts, even for the small teeth like bicuspids. Thus, the casts can be segmented with the struts and concavities in whole, and not partially sawed apart from the adjacent segments, resulting in maximum registration stability without mesial and distal movement, even for the small teeth like bicuspids. The bigger struts located at the hinge side are allocated for molars, and the smaller struts are for small teeth, like bicuspids, canines and anterior teeth. Bigger struts can be evenly spaced, wider apart, and smaller struts can be evenly spaced, narrower apart. Except for the presence of the registration struts and registration holes, the die-receiving surface 14 can be essentially flat and can form a stable planar base for receiving casting stone material thereon for forming a dental cast.

Referring to FIGS. 1–2 and 18, a hole 60 can be formed in one of the trays or arms, while a receiving area 62 can be formed in the other of the arms or trays. The hole 60 and receiving area 62 can be formed in a jointing area between the tray and the arms. A posterior vertical stop rod 64 can be received through the hole 60 and can abut to the receiving area 62. The posterior vertical stop rod 64 can be secured in the hole 60 so that the rod can increase stability for cases with non-supporting tooth abutment against the opposing cast.

While the above has described devices and methods suited for quadrant impression modeling, similar devices and methods can be configured for full-arch impression modeling, as shown in FIGS. 30a–c. All the characteristics found in quadrant upper tray 11 and lower tray 12 are reflected in a full-arch tray 90. The full-arch tray 90 can include upper and lower tray support members that are U-shaped to accept impression molds of the patient's entire mouth. The U-shaped tray 90 can be open through a middle of the U-shape, and can have an inner circumferential wall that is flat or straight from a bottom to a top, as shown in FIG. 30a and 30b, to facilitate removal of casting material, such as with a spatula while still wet.

A method for forming a dental model, and for using the system or devices 10 or 90 described above, includes forming a prepped model 15 of prepped teeth on the lower tray 12, and forming an opposing model 17 of opposing teeth on the upper tray 11, of a dental articulator 10 or 90. The prepped model 15 includes a model of a prepped tooth to receive a dental prosthesis, while the opposing model 17 includes a model of an opposite tooth opposite the prepped tooth. Forming the models 15 and 17 can include obtaining an impression 100 (FIG. 1b) of at least some of a patient's teeth. The impression 100 can typically be made by a dentist by placing a formable material onto a tray or the like, and having the patient bite into the formable material, thus leaving a negative impression of the patients teeth, as is known in the art. The impression includes a prepped side with an impression of the prepped tooth to receive a dental prosthesis, and an opposing side with an impression of the opposing tooth opposing the prepped tooth. Such an impression can typically be provided to the technician.

The impression can be disposed between the upper and lower trays 11 and 12 of the dental articulator 10 or 90.

Dental casting material can be introduced between the upper tray 11 and the opposing side of the impression 100 to form the opposing model 17 of the opposing tooth. For example, dental casting material can be disposed on the upper tray 11 and in the opposing side of the impression 100. The opposing side of the impression 100 can be disposed over the upper tray 11 so that dental casting material extends therebetween, and forms the opposing model 17 of the opposing tooth. The side of the impression 100 that has a prepared tooth typically faces the lower tray 12. Thus, regardless of whether the upper teeth or lower teeth are to receive a dental prosthesis, the lower tray 12 typically receives the prepped side of the impression 100.

Similarly, dental casting material can be introduced between the lower tray 12 and the prepped side of the impression 100 to form the prepped model 15 of the prepped tooth. For example, the dental casting material can be disposed on the lower tray 12 and in the prepped side of the impression 100. The lower tray 12 can be disposed over the prepped side of the impression 100 so that the dental casting material extends therebetween, and forms the prepped model 15 of the prepped tooth. The impression 100 can be removed from the dental articulator 10 or 100 leaving the opposing and the prepped models 17 and 15 on the respective upper and lower trays 11 and 12.

The impression 100 can first be inverted over the upper tray 11 and the opposing model 17 can be formed first. The impression 100 can then be inverted over the lower tray 12, while still attached to the opposing model 17 and upper tray 11, to form the prepped model 15. Thus, the resulting prepped and opposing models 15 and 17 can be mounted in the dental articulator with the bite exactly as the impression provided by the dentist. Alternatively, the prepped model can be formed first, and the opposing model can be formed after.

The prepped model 15 can be segmented on sides corresponding to the prepped tooth to form the prosthesis die 16. Thus, the upper and lower trays 11 and 12 receive respective upper and lower casts, or opposing and prepped models 17 and 15 (as shown in FIG. 20a). In practice, the dental technician cuts the cast 15 and/or 17 to separate out and form the master or prosthesis die 16 to be worked on. The model 15 and/or 17 can be cut into segments so that each segment has at least one registration pin 42 (or no pins at all if preferred), and at least two internally retentive cavities corresponding to at least two registration struts 56. Segments can be removed and reinserted into their precise location on the tray to reproduce the model of the original impression and the relationship of the upper and lower tray with respect to each other.

In accordance with one aspect of the invention, a dental articulator 10 or 90 can be obtained with upper and lower trays 11 and 12 pivotally coupled together by the hinge 20 that can be integrally formed with the trays. The hinge can include a first portion with a shoulder 24 substantially circumscribing a pivot axle 22, and a second portion with opposing fingers 26a and 26b movably disposed on opposite sides of the axle 22, and on opposite sides of the shoulder 24.

The lower and upper trays 11 and 12 can be pivoted about the hinge 20 that is integrally formed with the trays. Thus, the upper tray 12 can be pivoted to the open configuration to allow access to the prosthesis die 16. In addition, the upper tray 12 can be pivoted to the closed configuration to check for clearance between the dental prosthesis on the prosthetic die 16 and the opposing model 17.

In accordance with another aspect of the invention, a dental articulator 10 or 90 can be obtained with a thin membrane 44 or 44b extending across registration pin holes 40 and/or 41 in at least one of the trays, such as the lower tray 12. Registration pins 42 can be positioned in registration pin holes 40 and/or 41 in one of the trays, such as the lower tray 12. For example, at least one registration pin 42 can be positioned at a location corresponding to the prepped tooth and the prosthesis die 16. In addition, other registration pins can be positioned on either side of the prosthesis die 16. The pins can be located to the best advantage in working with the dental model. The registration pin 42 can be pressed through the thin membrane 44 and/or 44b extending across the registration pin hole 40 and/or 41 so that the registration pin breaks the thin membrane and extends through the thin membrane. As described above, the thin membrane can be positioned near the bottom of the registration pin hole, or at the top of the registration pin hole.

The prepped model 15 of the prepped tooth can be formed over the registration pin 42 on the tray 12 of the dental articulator. For example, the dental casting material can be poured over the registration pin 42. In addition, the dental casting material can be disposed over the registration pin holes 40 and/or 41 with the thin membrane 44 and/or 44b formed integrally with the tray and extending across the registration pin holes to resist dental casting material from substantially filling the registration pin holes.

In accordance with another aspect of the present invention, the dental casting material can be disposed around the registration struts 56 in at least one of the trays, such as the lower tray 12. As described above, the registration struts 56 can have a hexagonal cross section forming a hole in the prepped model 15 and the prosthesis die 16 that also has a hexagonal cross section. The hexagonal cross section of the struts and hole mate to resist movement of the prepped model 15 and the prosthesis die 16, and to properly orient and position the prepped model 15 and the prosthesis die 16 in the tray 12.

In accordance with another aspect of the present invention, the dental casting material can be disposed in at least one of the trays 11 and/or 12 with a trough formed by a perimeter wall 48 and/or 52. The perimeter wall 48 and/or 52 can have a wavy profile with a plurality of arcuate indentations. The wavy profile creates a mating wavy profile in the models 15 and 17 and the prosthesis die 16 to properly orient the models and die in the trays. In addition, the curved indentations form curved protrusions in the models 15 and 17 and die 16 that resist chipping, and thus resist debris interfering with the fit between the trays and the models and die.

The dental casting material can be disposed in the trays 11 and 12 and the impression 100 by pouring the dental casting material while it is in a semi-liquid state. After the dental casting material substantially hardens, dries, and/or solidifies, the impression 100 can be removed.

A "re-articulating" technique can be accomplished with the present system by softening the material of the arm by lightly heating one set of the articulating arms with a micro-torch and then setting the correct bite by hand while the articulating arms are still hot. The arms harden in the correct position as the material cools.

It is to be understood that the above-referenced arrangements are only illustrative of the application for the principles of the present invention. Numerous modifications and alternative arrangements can be devised without departing from the spirit and scope of the present invention. While the present invention has been shown in the drawings and fully described above with particularity and detail in connection with what is presently deemed to be the most practical and preferred embodiments(s) of the invention, it will be apparent to those of ordinary skill in the art that numerous modifications can be made without departing from, the principles and concepts of the invention as set forth in the claims.

What is claimed is:

1. A dental articulating device configured to duplicate at least a portion of a patient's mouth for use in producing a dental prosthesis, the device comprising:
   a) a pair of trays, pivotally coupled together, the trays pivoting with respect to one another between:
      i) a closed configuration, in which the trays are opposingly spaced-apart from one another; and
      ii) an open configuration, in which the trays are pivoted away from one another; and
   b) a pair of lower arms integrally formed with and extending from a lower tray;
   c) a pair of lower arms integrally formed with and extending from an upper tray:
   d) a pair of hinges, each disposed between a different one of the upper and the lower arms;
   e) the pair of hinges each being integrally formed with the arms and each including:
      i) a pivot axle, associated with one of the arms;
      ii) a shoulder, extending at least partially around the pivot axle and creating two axle portions extending on each side of the shoulder; and
      iii) a pair of opposing fingers, associated with another of the arms, with one of the pair of fingers contacting and extending at least partially about a first side of the axle while leaving a second side of the axle exposed, and with another of the pair of fingers contacting and extending about the second side of the axle while leaving the first side of the axle exposed; and
   f) wherein the pivot axles of the pair of hinges are collinear.

2. A device in accordance with claim 1, wherein each of the pair of fingers slidably bears against the axle and the shoulder.

3. A device in accordance with claim 1, wherein the axle is coupled to the tray by the shoulder.

4. A device in accordance with claim 1, wherein each of the pair of fingers is curved and includes a curvature oriented orthogonal to the pivot axle.

5. A device in accordance with claim 4, wherein the hinge further includes:
   a curved channel, circumscribing a portion of the pivot axle, and movably receiving one of the fingers therein.

6. A device in accordance with claim 1, wherein at least one of the dental trays further includes:
   a) an array of registration pin holes, formed in the dental tray, each configured to receive a registration pin; and
   b) a thin membrane, extending across the registration pin holes and closing off the registration pin holes, the thin membrane being piercable by a registration pin when inserted into the hole.

7. A device in accordance with claim 1, wherein at least one of the dental trays further includes:
   registration struts having a hexagonal cross section.

8. A device in accordance with claim 1, wherein at least one of the dental trays further includes:
   a trough formed by a perimeter wall, the perimeter wall having a wavy profile with a plurality of arcuate indentations.

9. The device of claim 1, wherein each of the pair of fingers extends no more than halfway around a circumference of the axle.

10. The device of claim 1, wherein the pair of fingers are disposed on opposite sides of the shoulder.

11. The device of claim 1, wherein the pair of fingers extend in opposite directions around a circumference of the axle.

12. The device of claim 1, wherein the pair of fingers are offset one from another along a length of the axle.

13. The device of claim 1, wherein the upper and lower arms extend outwardly from the trays to a width greater than a width of the trays.

14. A dental articulating device configured to duplicate at least a portion of a patient's mouth for use in producing a dental prosthesis, the device comprising:
   a) a pair of trays, pivotally coupled together, the trays pivoting with respect to one another between:
      i) a closed configuration, in which the trays are opposingly spaced-apart from one another; and
      ii) an open configuration, in which the trays are pivoted away from one another;
   b) each tray having a pair of arms, each arm extending rearwardly and outwardly with respect to the trays
   c) the pair of arms of each tray collectively defining an access opening therebetween, to allow an operator to access from a rear of the device objects disposed in or on the trays; and
   d) a pair of hinges, disposed between the pair of arms, each hinge including:
      i) a pivot axle collinear with respect to a pivot axle of the other hinge;
      ii) a shoulder, extending at least partially around the pivot axle and creating two axle portions extending on each side of the shoulder; and
      iii) a pair of fingers, associated with another of the trays, with two fingers pivotally positioned on opposite sides of the pivot axle and on opposite sides of the shoulder and separated by both the axle and the shoulder so that one of the pair of fingers is disposed on each side of the shoulder.

15. The device of claim 1, wherein one of the pair of upper arms includes a pivot axle and another of the pair of upper arms includes a pair of opposing fingers, to provide an offset configuration to the pair of upper arms.

16. A dental articulating device configured to duplicate at least a portion of a patient's mouth for use in producing a dental prosthesis, the device comprising:
   a) a pair of trays, pivotally coupled together, the trays pivoting with respect to one another between:
      i) a closed configuration, in which the trays are opposingly spaced-apart from one another; and
      ii) an open configuration, in which the trays are pivoted away from one another;
   b) each tray having a pair of arms, each arm extending rearwardly and outwardly with respect to the trays
   c) the pair of arms of each tray collectively defining an access opening therebetween, to allow an operator to access objects disposed in or on the trays; and
   d) a pair of hinges, disposed between the pair of arms, each hinge including:
      i) a pivot axle collinear with respect to a pivot axle of the other hinge;

ii) a shoulder, extending at least partially around the pivot axle and creating two axle portions extending on each side of the shoulder; and
iii) a pair of fingers, associated with another of the trays, with one of the pair of fingers contacting and extending at least partially about a first side of the axle while leaving a second side of the axle exposed, and with another of the pair of fingers contacting and extending about the second side of the axle while leaving the first side of the axle exposed.

\* \* \* \* \*